United States Patent [19]

Davison

[11] 4,446,866
[45] May 8, 1984

[54] MICROSURGICAL NEEDLE HOLDER

[75] Inventor: John A. Davison, San Jose, Calif.

[73] Assignee: Warner-Lambert Company, Morris Plains, N.J.

[21] Appl. No.: 356,676

[22] Filed: Mar. 10, 1982

[51] Int. Cl.³ .................. A61B 17/04; A61B 17/28
[52] U.S. Cl. .............................. 128/340; 81/428 R; 128/321
[58] Field of Search .................. 128/303, 321–324, 128/326, 340, 346, 354, 356; 81/43, 428 R; 294/16

[56] References Cited

U.S. PATENT DOCUMENTS 2,863,459 12/1958 Casper .............................. 128/321
3,407,816 10/1968 Curutchet ........................ 128/321 X
3,783,873 1/1974 Jacobs ............................. 128/303 R
4,392,494 7/1983 Ashby ................................ 433/4 X Primary Examiner—Dalton L. Truluck
Attorney, Agent, or Firm—Louis S. Gillow

[57] ABSTRACT

A microsurgical needle holder comprising a pair of arms which are pivotally mounted to each other, having needle holding jaws moving in opposition to each other in response to handles, at least one of the handles having an integral first handle extension and an attachable second handle extension adapted to receive weights at varying locations within said handle extensions, thereby providing for adjustment of the length and of the weight distribution of the microsurgical needle holder within the hand of the microsurgeon.

14 Claims, 6 Drawing Figures

U.S. Patent May 8, 1984 4,446,866
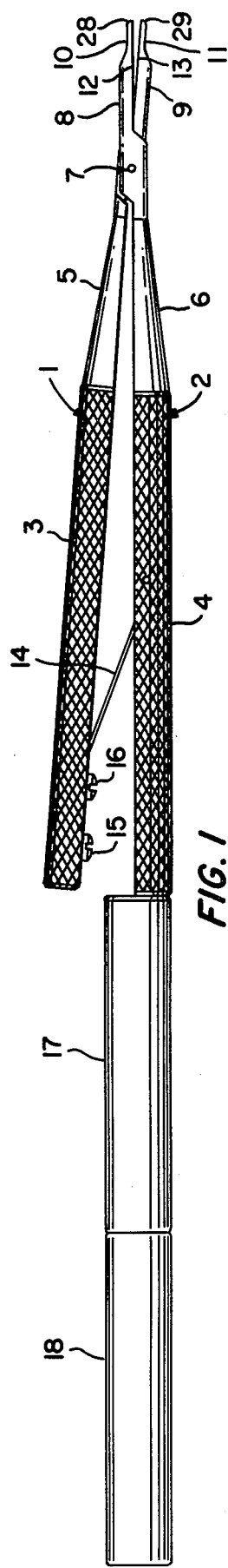
FIG. 1
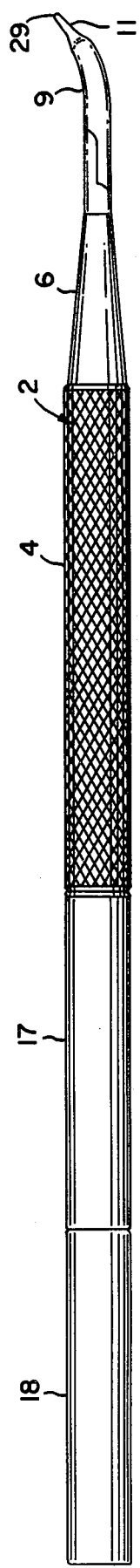
FIG. 2
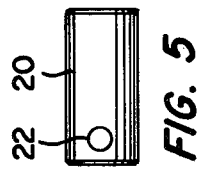
FIG. 4
FIG. 5
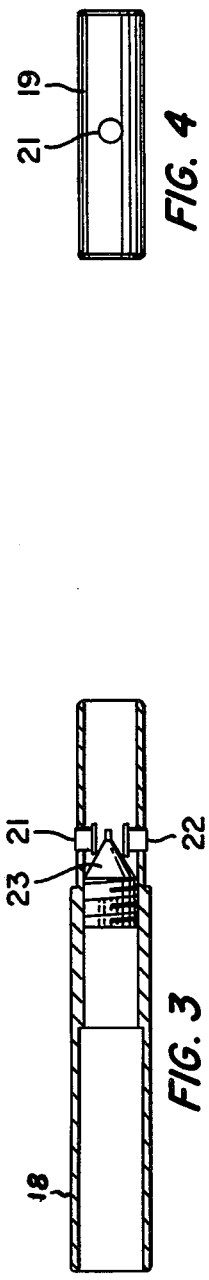
FIG. 3
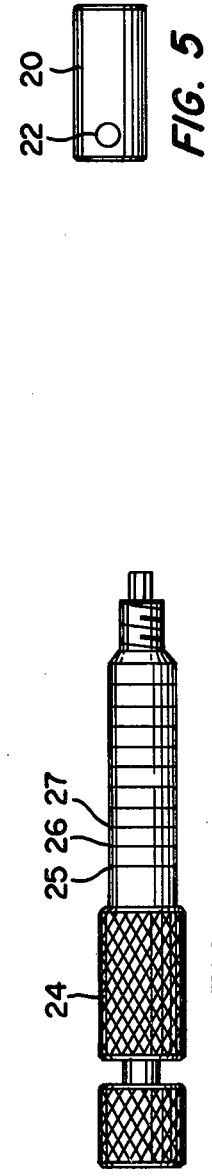
FIG. 6

MICROSURGICAL NEEDLE HOLDER

BACKGROUND OF THE INVENTION

Surgical needle holders in the prior art generally have a scissor handle configuration with a pair of opposing jaws to hold the needle.

Microsurgery is an ever expanding branch of surgery for new development in brain, heart and transplant operations where very small tissues, capillaries and nerves are required to be sutured. In order to minimize patient trauma the operations must be performed within a small body incision which requires multiple angle manipulation and precise control of the microsurgical needles and sutures. Some microsurgical operations are now so complex as to require teams of microsurgeons to operate continuously on a patient for periods of 6 to 18 hours.

It has been found that the prior art needle holders are generally unsatisfactory in microsurgery where very small needles and sutures must be precisely manipulated at multiple angles for extended time periods.

It is an object of the present invention to provide a microsurgical needle holder which may tightly grab and precisely manipulate a microsurgical needle and a microsurgical suture within a very small body incision.

It is another object of the present invention to provide a microsurgical needle holder wherein the length and the weight distribution are adjustable for each microsurgeon in order to maximize his dexterity in the precise manipulation of the microsurgical needles and sutures within the body incision and in order to minimize his fatigue during extended periods of microsurgery.

SUMMARY AND DETAILED DESCRIPTION

The objects of the present invention may be achieved by the microsurgical needle holder claimed herein, a preferred embodiment of which is the following drawings:

FIG. 1 is a plan view of the microsurgical needle holder having a first and second hollow cylindrical handle extension;

FIG. 2 is a side view of the microsurgical needle holder;

FIG. 3 is a cross-sectional view of the second hollow cylindrical handle extension for the microsurgical needle holder;

FIG. 4 is a plan view of an adjusting weight for mounting within either the first or the second hollow cylindrical handle extension of the microsurgical needle holder;

FIG. 5 is a plan view of another adjusting weight for mounting within either the first or the second hollow cylindrical handle extension of the microsurgical microsurgical needle holder; and FIG. 6 is a cross-sectional view of a positioner wrench for the second hollow cylindrical handle extension and for the adjusting weights.

Referring now to FIG. 1 and FIG. 2:

The preferred embodiment of the microsurgical needle holder of the present invention for use in small incisions in superficial and deep operations is approximately 3.5 to 4.5 inches in length and has a weight of approximately 1.5 to 2 ounces. The microsurgical needle holder comprises a pair of arms 1,2 each of which has a handle portion 3,4 a transition portion 5,6 a pivot 7 and a jaws portion 8,9. When the jaws 8,9 are closed by closing the handles 3,4 in scissors fashion, the microsurgical needle holder has a generally cylindrical configuration which is bisected by an axial plane into two arms 1,2 which join together on their flat bisected surfaces. The handles 3,4 have a diameter of approximately 0.35 to 0.4 inches and a length of approximately 3.50 to 3.75 inches so as to be easily held within the palm of one hand and rotated with the thumb and a finger thereof. The cylindrical surface of each handle 3,4 is knurled or otherwise roughened for better gripping and digital rotation. Integral with and intermediate the jaws 8,9, and the handles 3,4 are transition portions 5,6 of approximately 1.0 to 1.25 inches in length with a semicircular cross-section tapering from a diameter of approximately 0.375 inches to approximately 0.250 inches. The distal end away from the microsurgeon of the transition portion is further extended axially as jaws 8,9 for a length of approximately 1.25 inches with a semicircular cross-section diameter of approximately 0.250 inches. Integral with and at the distal end of the jaws 8,9 are jaw extensions 10,11 with a length of approximately 0.25 inches, with a semicircular cross-section diameter of approximately 0.024 inch and with final distal termination arcs 28,29 of approximately 0.024 inch diameter. The distal termination arcs 28,29 are in the flat plane of the jaw extension and with an arcuate range of approximately 0.02 to 0.03 inch diameter which is preferred for holding the microsurgical needle and suture at an acute angle for optimal manipulation within the incision. Each of the handles 3,4 with their integral transition portions 5,6, jaws 8,9 and jaw extensions 10,11 are axially aligned with their flat surfaces touching and joining together in conventional scissors fashion with a pivot 7 in the proximal portion of the jaws 8,9 so that the semi-cylindrical handles 3,4 are manually opened and closed causing the distal ends of jaws 8,9 and the jaw extensions 10,11 to correspondingly open and close flat upon a microsurgical needle or suture. The flat surfaces 12,13 of the jaws 8,9 and the jaw extensions 10,11 are preferably fabricated of antimagnetic cobalt bound tungsten carbide material, CA425 available from Carmet Corporation, Pittsburgh, Pa., or PM 12 available from Satellite Corporation, Kokomo, Ind. In an alternate embodiment the jaw flat surfaces 12,13 are removably affixed to the jaws 8,9 and the jaw extensions 10,11. Prior art needle holders either had smooth jaw flat surfaces or coarsely grooved flat surfaces accomplished by mechanical scouring so as to have up to approximately 10,000 grooves per square inch. Said prior art needle holders were found to be unsatisfactory with microsurgical needles and sutures because either the smooth surfaces did not grip sufficiently when wetted with body fluids or the coarsely grooved surfaces caused deformation of the fine needles and sutures. In the present invention, better gripping without deformation was obtained by finely cutting the jaw flat surfaces 12,13 with a diamond grinding wheel so as to produce grooves in the range of 16,600 to 110,000 grooves per square inch. Optimum results were obtained when each of the jaw flat surfaces 12,13 were grooved with intersecting ridges of approximately 62,500 V-shaped grooves per square inch at a depth of approximately 0.003 inches and a parallel separation of approximately 0.004 inches from tip to tip.

A leaf spring 14 is attached by screws 15,16 to a flat surface of one handle 3 near its proximal end and extending toward the distal end within the angle formed by the handles 3,4 so as to exert opening pressure on the handles when they are being closed by the microsurgeon.

One of the handles 4 is provided with a first hollow cylindrical handle extension 17 having a diameter of approximately 0.375 inches and a length of approximately 1.25 to 1.75 inches which is either integral with or attached to, and in axial alignment with the proximal end of the handle 4.

Referring now to FIG. 3:

Preferably, a second hollow cylindrical handle extension 18 having a diameter of approximately 0.375 inches and a length of approximately 1.25 to 1.75 inches is attached to, and in axial alignment with, the proximal end of the integral first hollow cylindrical handle extension 17. The second hollow cylindrical handle extension 18 extends back to rest within the cleft of the hand made by the forefinger and thumb in order to provide an enlarged surface for more precise control of the microsurgeon. In the hollow portion of the second hollow cylindrical handle extension 18 are two cylindrical locking pistons 21,22 extending from opposite sides of the cylindrical surfaces of the second handle extension 18 perpendicular to its axis and communicating with its cylindrical surfaces. Each of the locking pistons 21, 22 within the hollow interior of the second handle extension 18 is engaged by a conical bearing 23 in axial alignment with the second handle extension 18 and engaging with the locking pistons 21, 22 so that by depressing or retracting the conical bearing 23 the locking pistons 21,22 are respectively raised above and lowered below the cylindrical surfaces of the second handle extension 18 so as to be in locking contact with the internal surfaces of the first hollow cylindrical handle extension 17.

Referring now to FIG. 4 and FIG. 5:

Preferably, one or more hollow cylindrical weights 19,20 are provided for insertion within the first hollow cylindrical handle extension 17 and/or the second hollow cylindrical handle extension 18 in order to provide a range of variations in weight distribution of the microsurgical needle holder so as to give a better feel and balance within the hand of the microsurgeon. Preferably, two weights 19,20 are provided with an approximate weight of 0.25 and 0.5 ounces respectively, and having axial lengths of 0.5 inches and 1.0 inches, respectively. The weights 19,20 may be inserted either individually or together by locking pistons 21,22 at varying positions within the first hollow cylindrical extension 17 and/or the second hollow cylindrical handle extension 18 in order to provide the weight distribution desired by the microsurgeon.

Referring now to FIG. 6:

Preferably, the second hollow cylindrical handle extension 18 and the weights 19,20 are aligned along the axis within either the first or second hollow cylindrical handle extension 17,18 by a positioner wrench 24 engaging the conical bearing 23 within the second handle extension 18 and within the weights 19,20. The positioner wrench 24 has calibrations 25,26,27 along its axial length in order to attach the second handle extension 18 to the first handle extension 17 and to precisely position the weights 19,20 as desired by the microsurgeon.

It is to be understood that the present invention is not limited to the specific embodiments described and illustrated herein above. Inasmuch as various modifications and equivalents thereof, all within the scope of the invention, will become apparent to those skilled in the art. Therefore, the invention is limited only by the scope of the following claims:

What is claimed is:

1. A microsurgical needle holder comprising,
   a. a pair of arms pivotally mounted to each other intermediate their ends,
   b. opposed handles on the proximal ends of each of the arms on one side of the pivot,
   c. opposed jaws on the distal ends of each of the arms on the other side of the pivot,
   d. opposed flat textured surfaces on each of the jaws, said textured surfaces being substantially engageable to each other in clamping relationship when the handles are drawn together,
   e. at least one of said handles having an attachable first handle extension for increasing the length of said handle to be held within the palm while the other handle is being manipulated by the thumb and a finger of the microsurgeon, and
   f. at least one weight positionably engageable with said first handle extension for varying the center of balance of said microsurgical needle holder.

2. A microsurgical needle holder as cited in claim 1 further comprising
   a second handle extension attachable to said first handle extension and positionably engageable with said weight for further increasing the length of the handle within the palm of the microsurgeon and providing greater variance in the center of balance of said microsurgical needle holder.

3. A microsurgical needle holder comprising,
   a. the structure in accordance with claim 1 in which
   b. the first handle extension is hollow and is adapted to receive one or more weights at varying locations within its length for varying the weight distribution of the microsurgical needle holder within the hand of the microsurgeon.

4. A microsurgical needle holder comprising,
   a. the structure in accordance with claim 2 in which
   b. the second handle extension is hollow and is adapted to receive one or more weights at varying locations within its length for varying the weight distribution of the microsurgical needle holder within the hand of the microsurgeon.

5. A microsurgical needle holder comprising,
   a. the structure in accordance with claim 1 in which
   b. the jaws are tapered and curved to form a narrow arc at their distal ends for holding a microsurgical needle or suture at an acute angle.

6. A microsurgical needle holder comprising,
   a. the structure in accordance with claim 1 in which
   b. the flat clamping surfaces are grooved in in the range of 16,600 to 110,000 grooves per square inch.

7. A microsurgical needle holder comprising,
   a. the structure in accordance with claim 1 in which
   b. the flat clamping surfaces are grooved with V-shaped grooves of approximately 62,500 grooves per square inch.

8. A microsurgical needle holder according to claim 1 having a length of approximately 3.5 to 4.5 inches.

9. A microsurgical needle holder according to claim 1 having a weight of approximately 1.5 to 2.0 ounces.

10. A microsurgical needle holder according to claim 5 wherein the arc at the distal end of the jaws has a diameter of approximately 0.02 to 0.03 inches.

11. A microsurgical needle holder according to claim 1 wherein the handles have a diameter of approximately 0.35 to 0.4 inches.

12. A microsurgical needle holder according to claim 2 wherein the attachable second handle extension has a length of approximately 1.25 to 1.75 inches.

13. A microsurgical needle holder according to claim 2 wherein the attachable second handle extension has a weight of approximately 0.5 to 1.0 ounces.

14. A microsurgical needle holder according to claim 3 wherein the weights are in increments of approximately 0.25 ounces.

* * * * *